United States Patent
Akutsu et al.

(10) Patent No.: US 6,780,398 B1
(45) Date of Patent: Aug. 24, 2004

(54) AQUEOUS NASAL FORMULATION

(75) Inventors: Rika Akutsu, Imaichi (JP); Kenji Hosoya, Imaichi (JP); Koho Kawamura, Imaichi (JP); Yasuhiro Mishima, Imaichi (JP); Tomohisa Onozaki, Imaichi (JP); Nobuya Sugibayashi, Imaichi (JP)

(73) Assignee: Glaxo Smithkline Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/049,167
(22) PCT Filed: Aug. 3, 2000
(86) PCT No.: PCT/JP00/05200
§ 371 (c)(1),
(2), (4) Date: May 16, 2002
(87) PCT Pub. No.: WO01/10409
PCT Pub. Date: Feb. 15, 2001

(30) Foreign Application Priority Data

Aug. 7, 1999 (GB) ............................................. 9918559

(51) Int. Cl.$^7$ ............................ A61K 9/12; A61K 31/58
(52) U.S. Cl. ............................ 424/45; 424/46; 424/434; 424/493; 514/853
(58) Field of Search ............................ 424/45, 46, 434, 424/493; 514/853

(56) References Cited

FOREIGN PATENT DOCUMENTS

| EP | 0 780 127 A | 6/1997 |
| WO | 97 46243 A | 12/1997 |
| WO | 99 49984 A | 10/1999 |

OTHER PUBLICATIONS

"Aldecin Nasal Spray," Medical Journal of Australia, vol. 2, No. 9, 1979, p. 494 XP000971559 p. 494, Column 3.

*Primary Examiner*—Thurman K. Page
*Assistant Examiner*—Mina Haghighatian
(74) *Attorney, Agent, or Firm*—James P. Riek

(57) ABSTRACT

An aqueous nasal formulation comprising beclomethasone dipropionate anhydrate for use in the treatment of respiratory disorders.

16 Claims, 5 Drawing Sheets

CHALLENGE TEST OF BANS AGAINST PS. CEPACIA

|  | $LOG_{10}$ INNOCULUM COUNT | $LOG_{10}$ REDUCTION* | | | |
|---|---|---|---|---|---|
|  |  | 2 DAYS | 7 DAYS | 14 DAYS | 28 DAYS |
| BKC 0.02% w/w | 6.2 | 0.3 | 1.0 | 1.3 | 1.8 |
| PEA 0.275% v/w | 6.2 | 0.2 | 0.6 | 1.7 | NR |
| BKC 0.02% w/w + PEA 0.275% v/w | 6.2 | NR | NR | NR | NR |

*: $LOG_{10}$ REDUCTION = $LOG_{10}$ (INNOCULUM COUNT) - $LOG_{10}$ (SAMPLE COUNT)
NR: NO RECOVERY

AQUEOUS NASAL FORMULATION

This application is filed pursuant to 35 U.S.C. §371 as a United States National Phase Application of International Application No. PCT/JP00/05200 filed 3 Aug., 2000, which claims priority from GB 9918559.7 filed 7 Aug. 1999 in the United Kingdom.

The present invention relates to an aqueous nasal formulation for use in the treatment of respiratory disorders.

Aerosol formulations are commonly used as effective anti-inflammatory treatments, but have implications with environmental safety. The most commonly used propellants in such formulations were previously chlorofluorocarbon containing (or CFC) propellants, however, these are currently being phased out, following the 1987 Montreal Protocol Agreement.

Since then, safer hydrogen containing fluorocarbons have been used as propellants in aerosol formulations, but these are relatively expensive and the environmental impact of these new propellants has also been questioned.

Thus, there is a need for safe anti-inflammatory treatments such as aqueous nasal formulations. The corticosteroid beclomethasone dipropionate (9α-chloro-16β-methyl-1, 4-pregnadiene-11α, 17α, 21-triol-3, 20-dione-17,α21-dipropionate) is well known as a topical anti-inflammatory steroid and is found in aqueous nasal formulations.

Prior aqueous nasal formulations containing beclomethasone dipropionate, used in treating such indications as allergic rhinitis (such as Beconase™AQ) have utilised beclomethasone dipropionate monohydrate in addition to the following constituents:

Anhydrous dextrose;
Avicel RC591 (Microcrystalline cellulose and carboxymethylcellulose sodium);
Phenylethyl alcohol;
Benzalkonium chloride;
Polyoxyethylene (20) sorbitan monooleate; and purified water Beclomethasone dipropionate monohydrate is not currently licensed in all territories of the world (notably not in Japan) and as a consequence, nasal formulations containing such a medicament cannot be marketed in such territories without substantial research effort and expense. However, there is an alternative anhydrous form of beclomethasone dipropionate, previously used in a nasal formulation (eg. Aldecin™ AQ) which contains the following constituents:

Micronised beclomethasone dipropionate anhydrate;
Avicel RC591 (Microcrystalline cellulose and carboxymethylcellulose sodium);
Glycerol;
Propylene glycol:
Polyoxyethylene (20) sorbitan monooleate; and purified water.

However, in the absence of a sealed pressurised container, as with the propellant based delivery systems, these formulations may be prone to contamination. As a consequence, potentially harmful bacteria may contaminate the formulation and then be inhaled directly into the nasal cavity. Additionally, these formulations have also been known to cause irritancy, which is especially undesirable in respect of paediatric treatment.

Thus, according to the present invention we provide a pharmaceutical formulation which comprises an aqueous solution of carboxy methylcellulose sodium, glycerol, propylene glycol and polyoxyethylene (20) sorbitan monooleate, containing suspended therein particulate microcrystalline cellulose and beclomethasone dipropionate anhydrate characterised in that said aqueous suspension further comprises:

Dextrose;
Phenylethyl alcohol;
Benzalkonium chloride;
Disodium hydrogen orthophosphate; and
Citric acid The presence of dextrose, disodium hydrogen orthophosphate and citric acid is intended to overcome the irritancy problems associated with current anhydrous beclomethasone dipropionate formulations. This improvement is believed to be mediated through the dextrose acting as an isotonicity adjusting agent. Furthermore, the beclomethasone dipropionate anhydrate may be stabilised by appropriate selection of pH using disodium hydrogen orthophosphate and citric acid to act as a buffer.

In addition, phenylethylalcohol and benzalkonium chloride are present within the formulation to act as preservatives.

Dextrose is preferably used as dextrose anhydrous. Disodium hydrogen orthophosphate is preferably used as disodium hydrogen orthophosphate anhydrous. Citric acid is preferably used as citric acid monohydrate. Microcrystalline cellulose and carboxy methylcellulose sodium is preferably used as the branded product Avicel RC591 (which typically contains 87–91% microcrystalline cellulose and 9–13% carboxy methylcellulose sodium).

Particulate beclomethasone dipropionate anhydrate will suitably be micronised and have a mean particle size less than 20$\mu$m, preferably less than 10$\mu$m, especially 1–5$\mu$m. Particulate microcrystalline cellulose will preferably have a particle size in the range 1 to 100$\mu$m.

A pharmaceutically acceptable amount of micronised beclomethasone dipropionate anhydrate is present within the formulation, which is preferably between 0.025–0.25% (w/w), especially 0.1% (w/w). The branded product Avicel RC591 and propylene glycol are suspending agents and are desirably added in a suitable amount to achieve this function, preferably between 1–5% and 0.1–20% (w/w) respectively, especially 1.5% and 1.0% (w/w) respectively.

We believe that Avicel RC591 acts as a suspending agent by imparting thixotropic properties to the formulation, wherein the formulation may become a stable suspension upon being stirred, shaken or otherwise disturbed. We similarly believe that propylene glycol aids stabilization of the formulation by reducing the bubbles which arise due to the presence of Avicel RC591 and benzalkonium chloride in the formulation.

Glycerol is added in a suitable amount to achieve its desired function as an excipient which reduces the solubility of beclomethasone dipropionate anhydrate in formulation; preferably the amount of glycerol will be such as to make the beclomethasone dipropionate anhydrate essentially insoluble in the formulation. An amount of glycerol which is preferably between 0.1–6% (w/w), especially 4.0% (w/w) will be suitable. The wetting agent, polyoxyethylene (20) sorbitan monooleate (typically supplied as the branded product Polysorbate 80) is desirably added in a sufficient quantity to achieve this function, preferably between 0.001–0.01% (w/w), especially 0.007% (w/w). The components disodium hydrogen orthophosphate anhydrous and citric acid monohydrate, which act as buffers, are desirably added in a suitable amount to achieve a final pH, following adjustment if necessary, of between 5 and 6, especially 5.5. Suitable concentrations of each component are 0.01–0.4% and 0.01–0.2% (w/w) respectively, especially 0.31% and 0.2% (w/w) respectively. Dextrose anhydrous is an isotonicity adjusting agent and is added in a suitable amount to achieve isotonicity with fluids of the nasal cavity. Suitable concentrations are between 0.1 and 5% (w/w), especially 5.0% w/w. Phenylethyl alcohol and benzalkonium chloride are preservatives which are preferably added in concentrations between 0.001–1% (v/w) and 0.001–1% (w/w) respectively, especially 0.275% (v/w) and 0.02% (w/w), respectively.

Besides its very good antiallergic properties and the above mentioned reduction in irritancy, the benefits of the invention may include the following:

Surprisingly, we have found that phenylethylalcohol has preservative properties by killing *Pseudomonas cepacia* (now known as *Burkhoderia cepacia*) by a synergistic effect with benzalkonium chloride. *Ps. cepacia* is a bacterium which is capable of opportunistic infections such as blood poisoning and due to the bacterium being largely resistant to antibiotics, clinical treatment is complex. Results demonstrating this effect are shown in FIG. 7.

A formulation of the present invention may be prepared by the manufacturing process according to the flow diagram shown in FIG. 1.

A typical container suitable for a formulation of the present invention may be of the type exemplified in FIGS. 2 and 3. As a further aspect of the present invention we provide a container comprising a pharmaceutical formulation according to the present invention suitable for delivering it in the form of a nasal spray.

A suitable dosing regime for the formulation of the present invention would be for the patient to inhale deeply subsequent to the nasal cavity being cleared. During inhalation the formulation would be applied to one nostril while the other is manually compressed. This procedure would then be repeated for the other nostril.

Wherein the patient is adult, two inhalations would be administered by the above procedure (100μg beclomethasone dipropionate anhydrate in total) four times each day.

Wherein the patient is a child, two inhalations would be administered by the above procedure (100μg beclomethasone dipropionate anhydrate in total) two times each day.

It will be appreciated that the above dosing regime should be adjusted according to the patient's age, body weight and/or symptom severity. However, the maximum daily dose should not exceed 16 inhalations for an adult and 8 inhalations for a child. If remission of the nasal symptoms is observed, the dose should be decreased as appropriate.

Examples of disease states in which the formulation of the present invention has potentially beneficial anti-inflammatory effects include allergies associated with the nasal cavity, more particularly allergic rhinitis.

Thus, according to a further aspect of the invention we provide a pharmaceutical formulation of the present invention for use in the treatment or prophylaxis of allergic rhinitis.

We also provide a use of a pharmaceutical formulation of the present invention in the manufacture of a medicament for the treatment or prophylaxis of allergic rhinitis.

More specifically, the formulation of the present invention may be illustrated by reference to the following example:

EXAMPLE 1

A solution of propylene glycol (0.3 kg) in purified water (23.6 kg) is dispersed by mixing at 2000 rpm for 5 mins. To this solution, dextrose anhydrate (1.5 kg), phenylethyl alcohol (82.5 g) and microcrystalline cellulose and carboxymethylcellulose sodium (Avicel RC591; 0.45 kg) is then added separately and mixed for a further 10, 5 and 30 mins, respectively. The dispersing is then ceased and the mixture is allowed to stand for 60 mins to hydrate. Dispersion is resumed at 3000 rpm for 10 mins and then re-adjusted to 2000 rpm.

Anhydrous disodium hydrogen orthophosphate (93 g) is added to purified water (1.8 kg) and dissolved by mixing at 3000 rpm for 15 mins. This solution is then mixed into the dispersing suspension for 5 mins as is a solution of citric acid, prepared by manually mixing citric acid (0.06 kg) with purified water (600 g).

Glycerol (1.2 kg) was heated at 48° C.±2° C. and polyoxyethylene (20) sorbitan monooleate (Polysorbate 80; 2.1 g) is then dissolved in the glycerol. A slurry is then formed by mixing micronised beclomethasone dipropionate anhydrate (30 g) with the glycerol and polyoxyethylene (20) sorbitan monooleate solution at 4500 rpm at 48° C.±2° C. for 30 mins. This slurry is then added to the dispersing suspension and mixed for 15 mins.

A solution of benzalkonium chloride (50% w/v; 11.82 g) is then diluted with purified water (220g), heated to 35–40° C. and then mixed with the drug suspension for 3 mins. Dispersion is then ceased, pH is adjusted to that of an optimum value, typically between 5 and 6, especially 5.5. The drug suspension is then filtered through 100 mesh filters and stored prior to filling into clean bottles. This procedure results in the components being present in the following concentrations:

| | |
|---|---|
| Micronised beclomethasone dipropionate anhydrate | 0.1% (w/w) |
| Dextrose anhydrous | 5.0% (w/w) |
| Microcrystalline cellulose and carboxymethylcellulose sodium (Avicel RC591) | 1.5% (w/w) |
| Phenylethyl alcohol | 0.275% (v/w) |
| Benzalkonium chloride solution 50% (w/v) | 0.04% (v/w) |
| Glycerol | 4.0% (w/w) |
| Propylene glycol | 1.0% (w/w) |
| Polyoxyethylene (20) sorbitan monooleate | 0.007% (w/w) |
| Disodium hydrogen orthophosphate anhydrous | 0.31% (w/w) |
| Citric acid monohydrate | 0.2% (w/w) |
| Purified water | to 100%. |

Biological Data

The formulation of the present invention, Example 1 (beclomethasone dipropionate anhydrate aqueous nasal spray, hereinafter defined as BANS) which delivers 50 μg BDP in a single spray was tested in a variety of assays to deduce its effect upon nasal symptoms when compared with controls and a prior art formulation (Aldecin™ AQ).

1 Effect of BANS on TDI-induced Nasal Symptoms in Sensitised Guinea Pigs.

Guinea pigs were immunised by 2×5 days intranasal application of 10% TDI (toluene 2, 4-diisocyanate) at intervals of 3 weeks. One or two weeks after the final sensitisation, a nasal allergy like response (sneeze, rhinorrhea, nasal obstruction) was provoked by intranasal application of 5% TDI. Drugs were topically applied 0.5, 1 or 4 hr before the provocation (1 spray each nostril equivalent to 100 μg BDP), however, a control utilised animals sensitised with 5% TDI without drug treatment. Any nasal symptoms were then observed (eg. sneezing, rhinorrhea and nasal obstruction) and scored according to the criteria displayed in Table 1.

TABLE 1

Criteria used to assign a nasal symptom score for each group

| | Score | | | |
|---|---|---|---|---|
| Symptom | 0 | 1 | 2 | 3 |
| Sneezing | Not observed | 1–4 | 5–11 | >12 |
| Watery rhinorrhea | Dry nostril | Snivel observed, but remains within nostril | Snivel leaks from nostril and wets the nasolabial portion, but does not discharge | Snivel drops from the nose |
| Nasal obstruction | Not observed | Observed | — | — |

The sum of the score was regarded as the nasal response of the animal and a 'mean score' value was given for the mean of the scores of each group. The results of this investigation are shown in FIG. 4.

2) Effect of BANS on Antigen Induced Nasal Vascular Permeability in Sensitised Rats.

Rats were immunised with DNP-As and the animals with 72 hr-PCA titre over x50 were used. Under the anaesthesia, the nasal cavity of the rat was perfused with saline. After the dye (4% pontamine sky blue (Brilliant blue) 5 ml/kg) was intravenously injected, the perfusate was collected for 10 min. Thereafter, the antigen solution was perfused for 10 min followed by perfusion with saline for further 30 min. The dye concentration of the perfusate collected was determined by absorbance at 616nm. Drugs were topically applied 24hr and 1hr before the provocation (2 sprays at each time equivalent to 100µg BDP). Controls were prepared which utilised antigen challenged sensitised animals without drug treatment (control) and BANS placebo treatment (vehicle). The results of this investigation are shown in FIG. 5.

3) Effect of BANS on the Increase in Intranasal Pressure After Antigen Challenge in Sensitised Guinea Pigs.

Guinea pigs were immunised with OVA by subcutaneous administration in mixture with FCA. The animals with 4 hr-PCA titre over x50 were used. Under the anaesthesia, a Y-shaped cannula was inserted into the trachea of larynx side. One end of the cannula was connected to the transducer to measure intranasal pressure and the other end to air bomb to supply contact flow of the air. After instillation of the antigen solution into the nose, intranasal pressure was measured for 28 min. Drugs were topically applied 24 hr and 1 hr before the provocation (4 sprays at each time equivalent to 200 µg BDP). Controls were prepared which utilised antigen challenged sensitised animals without drug treatment (control) and BANS placebo treatment (vehicle). The results of this investigation are shown in FIG. 6.

4) Challenge Test of BANS Against *Ps. Cepacia*

Formulations corresponding to BANS and the same formulation containing only 0.02% (w/w) benzalkonium chloride as preservative (i.e. no phenylethyl alcohol) and the same formulation containing only 0.275% (v/w) phenylethylalcohol as preservative (i.e. no benzalkonium chloride) were challenged with an innoculum of *Ps cepacia*. The results, shown in FIG. 7, demonstrate that the combined preservative is much improved in respect of antimicrobial effectiveness relative to the two preservatives individually in this formulation.

ABBREVIATIONS

Figure 1:
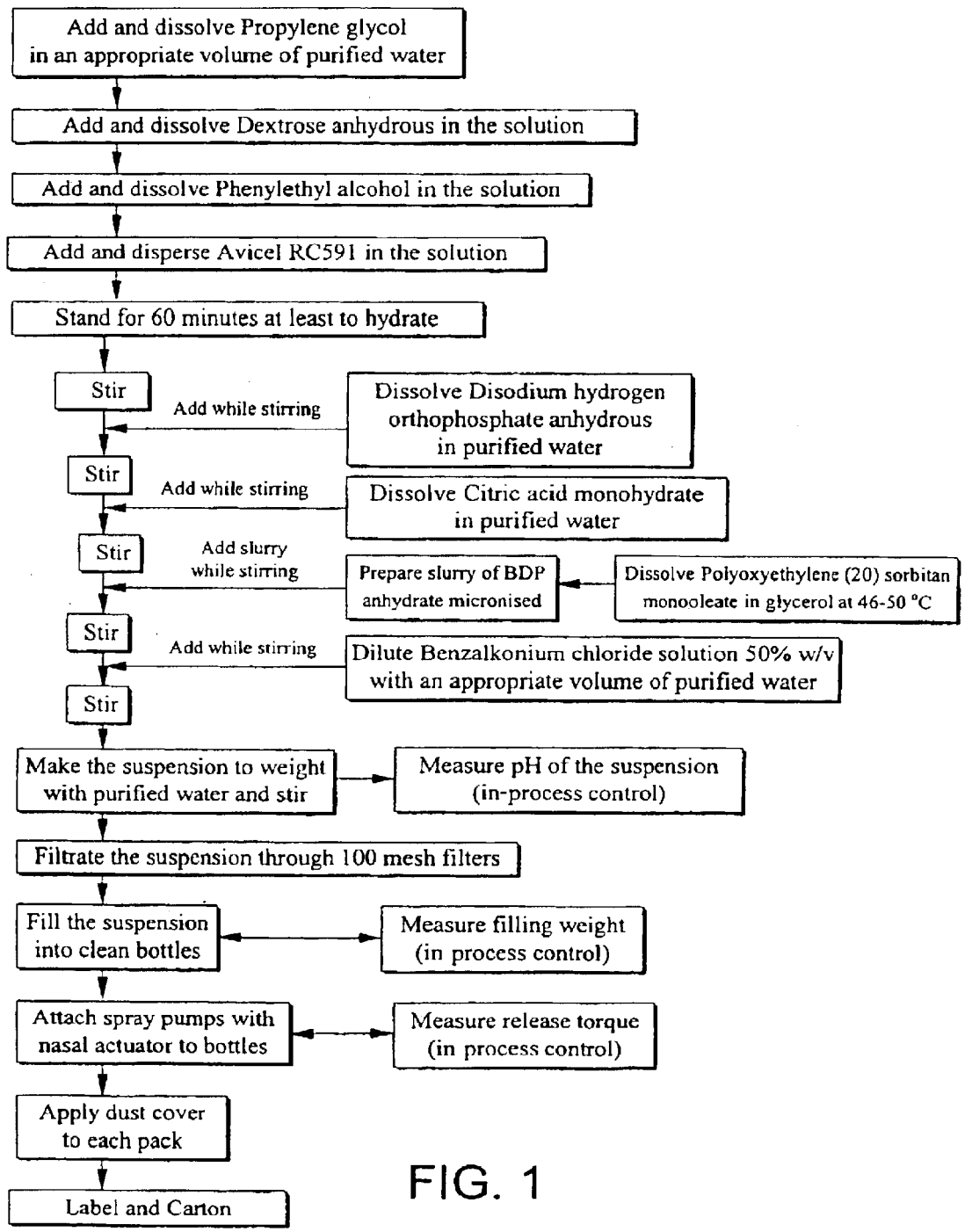
FIG. 1 contains a flow diagram to clearly describe the manufacturing process involved to produce a formulation of the present invention.
Figure 2:
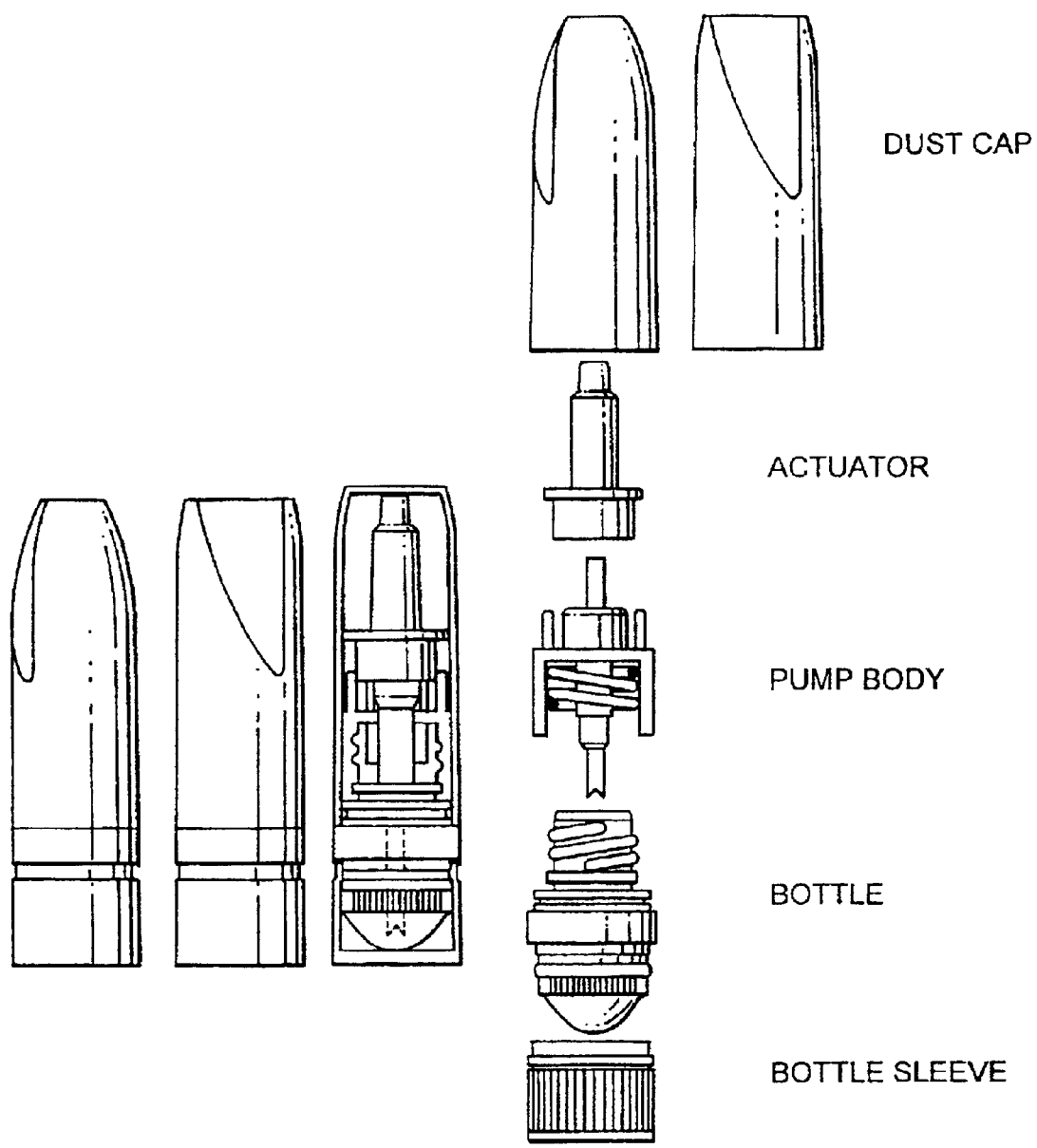
FIG. 2 contains a cross section description of a suitable container for the formulation of the present invention.
Figure 3:
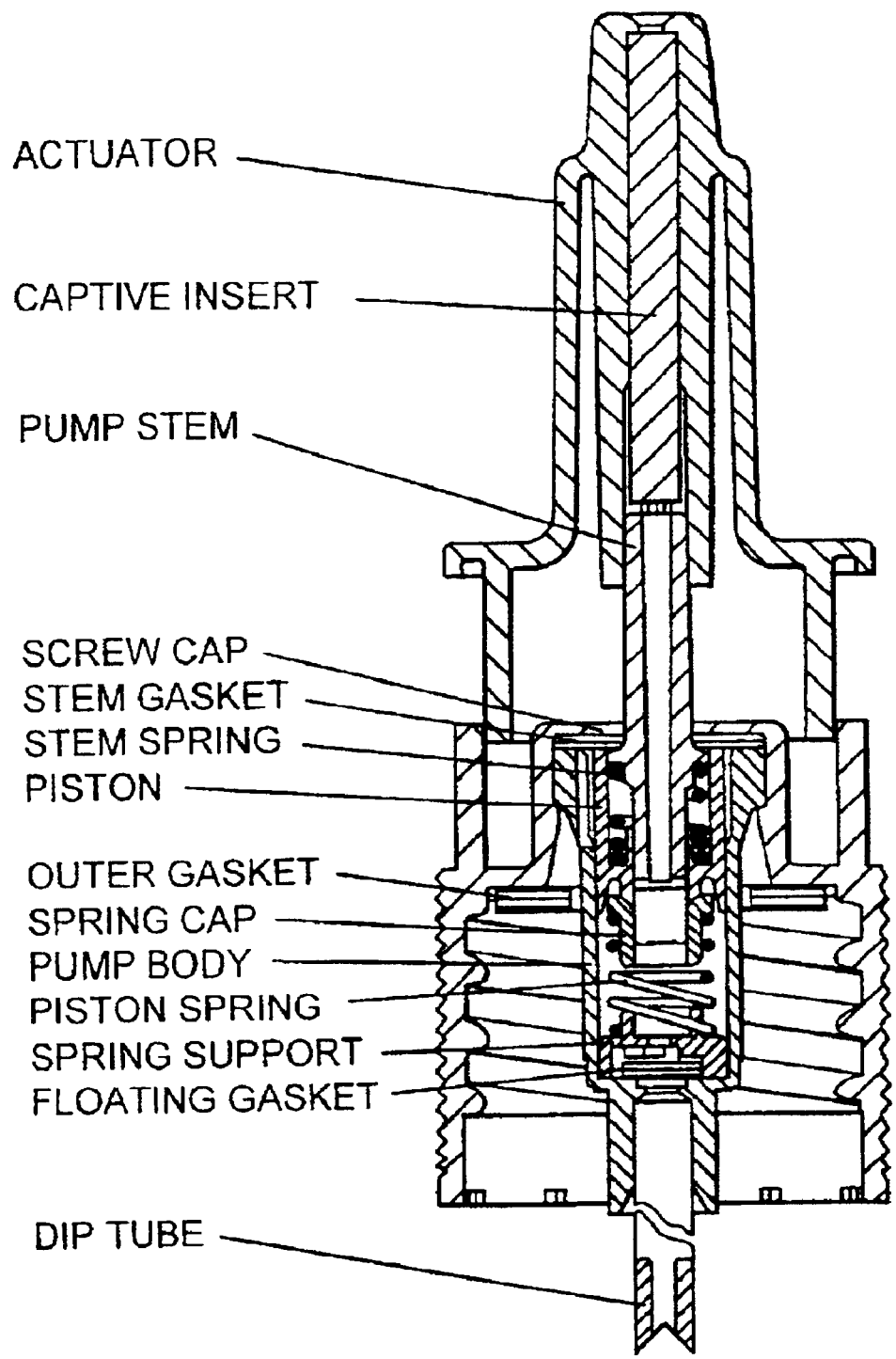
FIG. 3 contains a cross section diagram of a pump system (Valois VP3/50) with actuator suitable for use in a container such as that described in FIG. 2.
Figure 4:
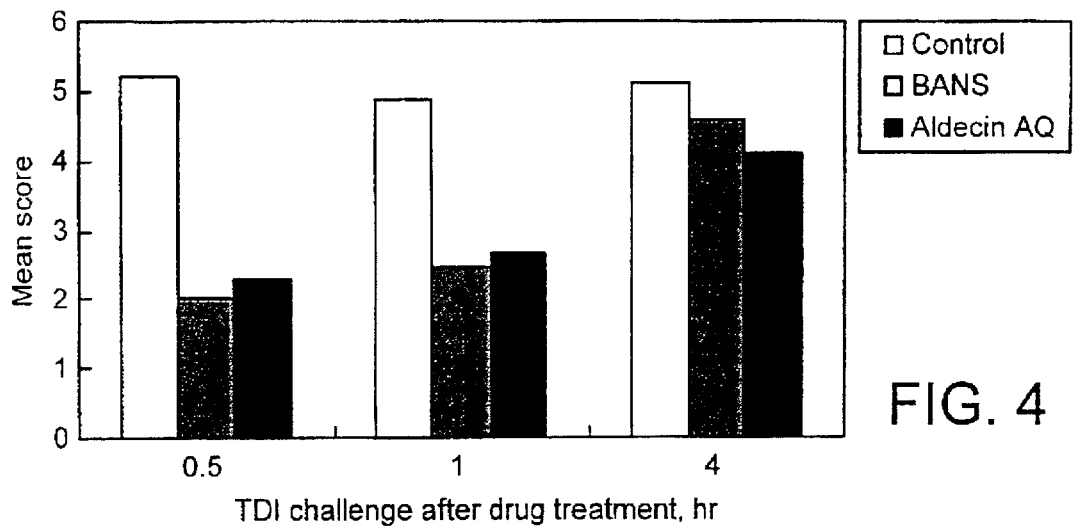
FIG. 4 compares the effect of BANS, Aldecin™ AQ and a control upon TDI-induced nasal symptoms at differing time intervals from drug administration.
Figure 5:
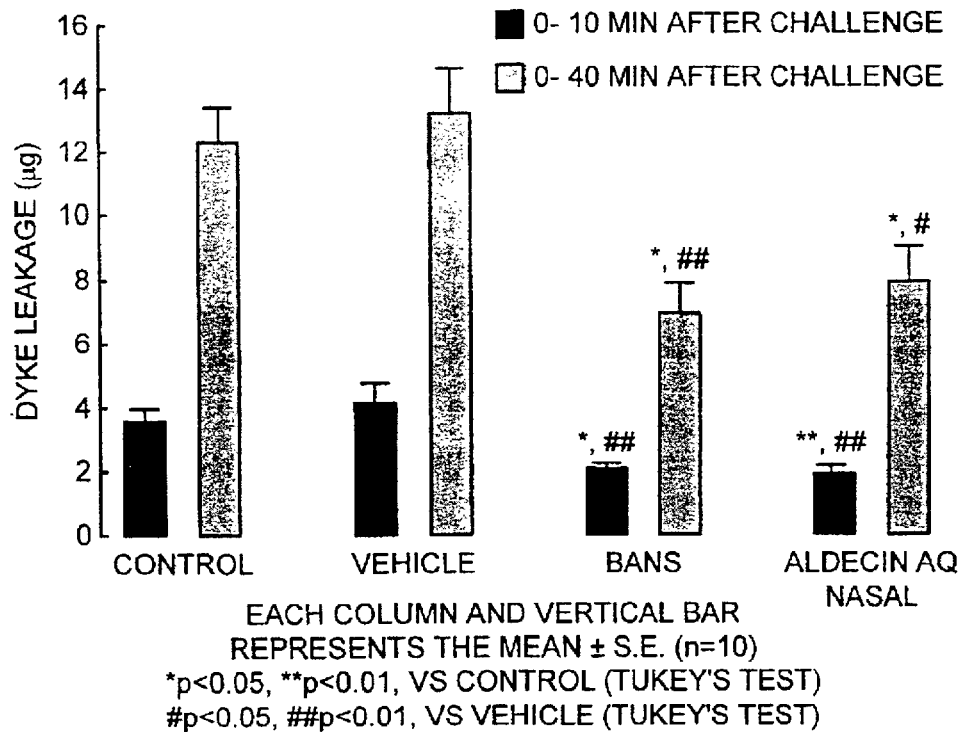
FIG. 5 compares the effect of BANS, Aldecin™ AQ, a vehicle and a control upon antigen induced nasal vascular permeability at a suitable time from drug administration.
Figures 6, 7:
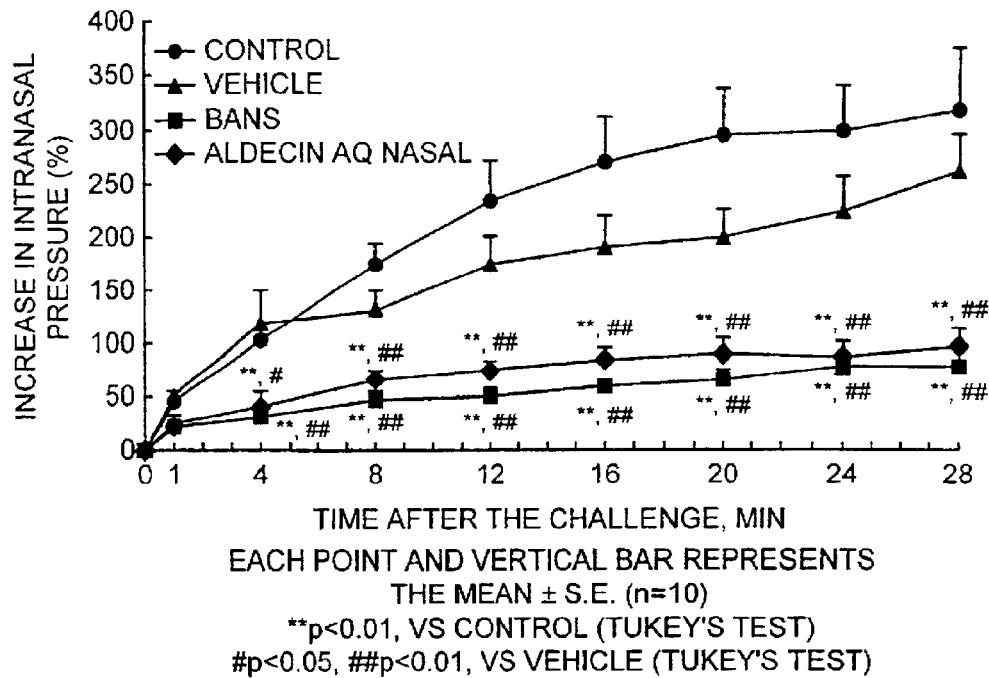
FIG. 6 compares the effect of BANS, Aldecin™ AQ, a vehicle and a control upon the increase in intranasal pressure from 0 to 28 minutes after antigen challenge.
FIG. 7 shows the results of the challenge test of BANS and the same formulation without one of each of the two preservatives against *Ps. cepacia*.

| | |
|---|---|
| BANS | beclomethasone dipropionate anhydrate aqueous nasal spray (following Example 1, except where indicated) |
| BDP | beclomethasone dipropionate |
| TDI | toluene 2,4-diisocyanate |
| FCA | Freund complete adjuvant |
| PCA | Passive cutaneous anaphylaxis |
| DNP-As | Ascari's suum extracts conjugated with dinitrophenol (antigen) |
| OVA | Ovalbumin (antigen) |
| BKC | Benzalkonium chloride |
| PEA | Phenylethyl alcohol |

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

What is claimed is:

1. A Pharmaceutical formulation which comprises an aqueous solution of carboxy methylcellulose sodium, glycerol propylene glycol and polyoxyethylene (20) sorbitan monooleate, containing suspended therein particulate microcrystalline cellulose and beclomethasone dipropionate anhydrate, characterised in that said aqueous suspension further comprises:

Dextrose;

Phenylethyl alcohol;

Benzalkonium chloride;

Disodium hydrogen orthophosphate; and

Citric acid.

2. A pharmaceutical formulation according to claim 1 characterised in that it is buffered to a pH of between 5 and 6.

3. A pharmaceutical formulation according to claim 1 characterised in that it is isotomic with fluids of the nasal cavity.

4. A pharmaceutical formulation according to claim 1 having a composition as follows:

| | |
|---|---|
| Micronised beclomethasone dipropionate anhydrate | 0.1% (w/w) |
| Dextrose anhydrous | 5.0% (w/w) |

-continued

| | |
|---|---|
| Microcrystalline cellulose and carboxymethylcellulose sodium (Avicel RC591) | 1.5% (w/w) |
| Phenylethyl alcohol | 0.275% (v/w) |
| Benzalkonium chloride solution 50% (w/v) | 0.04% (v/w) |
| Glycerol | 4.0% (w/w) |
| Propylene glycol | 1.0% (w/w) |
| Polyoxyethylene (20) sorbitan monooleate | 0.007% (w/w) |
| Disodium hydrogen orthophosphate anhydrous | 0.31% (w/w) |
| Citric acid monohydrate | 0.2% (w/w) |
| Purified water | to 100%. |

5. A container comprising a pharmaceutical formulation according to claim 1 suitable for delivering it in the form of a nasal spray.

6. A pharmaceutical formulation according to claim 1 for use in the treatment or prophylaxis of allergic rhinitis.

7. A method for the manufacture of a medicament product useful in the treatment of prophylaxis of allergic rhinitis comprising the step of incorporating a pharmaceutical formulation according to claim 1 in said medicament product.

8. A method of treatment of allergic rhinitis which comprises administering to a patient a pharmaceutically acceptable amount of a formulation according to claim 1.

9. A process for preparing a formulation according to claim 1, comprising the steps of:
   a. dissolving propylene glycol in water to produce a liquid formulation 1;
   b. dissolving dextrose in liquid formulation 1 to generate liquid formulation 2;
   c. dissolving phenylethyl alcohol in liquid formulation 2 to generate liquid formulation 3;
   d. dispersing Avicel RC591 in liquid formulation 3 to generate liquid formulation 4;
   e. providing disodium hydrogen orthophosphate anhydrous dissolved in water;
   f. providing citric acid monohydrate dissolved in water;
   g. providing a slurry of micronized beclomethasone dipropionate anhydrate in polyoxyethelene (20) sorbitan monooleate dissolved in glycol;
   h. providing benzalkonium chloride dissolved in water;
   i. adding the products of steps e, f, g, and h, under agitation, to a liquid formulation comprising the contents of liquid formulation 4 to yield a liquid formulation 5.

10. The process of claim 9, wherein liquid formulation 4 is permitted to stand for at least 60 minutes to allow for hydration.

11. The process of claim 9, wherein the slurry of micronized beclomethasone dipropionate anhydrate in polyoxyethylene (20) sorbitan monooleate dissolved in glycerol, is prepared by dissolving said polyoxyethylene (20) sorbitan monooleate in glycol, and adding micronised beclomethasone dipropionate anhydrate thereto.

12. The process of claim 11, wherein the polyoxyethylene (20) sorbitan monooleate is dissolved in the glycol at between 46–50° C.

13. The process of claim 9, wherein said benzalkonium chloride dissolved in water is presented in a 50% w/v solution.

14. The process of claim 9, wherein said liquid formulation 5 is subjected to a pH measurement, and if required the pH is adjusted to between 5 and 6 to generate a liquid formulation 6.

15. The process of claim 9, wherein said liquid formulation 6 is passed through at least one 100 mesh filter, to generate a liquid formulation 7.

16. The process of claim 15, wherein said liquid formulation 7 is metered into a suitable delivery device.

* * * * *

UNITED STATES PATENT AND TRADEMARK OFFICE
CERTIFICATE OF CORRECTION

PATENT NO. : 6,780,398 B1
DATED : August 24, 2004
INVENTOR(S) : Rika Akutsu et al.

It is certified that error appears in the above-identified patent and that said Letters Patent is hereby corrected as shown below:

Column 6,
Line 59, replace "isotomic" with -- isotonic --.

Signed and Sealed this

Twenty-fourth Day of May, 2005

JON W. DUDAS
*Director of the United States Patent and Trademark Office*